United States Patent

Jouquey et al.

Patent Number: 4,632,820
Date of Patent: Dec. 30, 1986

[54] NOVEL RADIOACTIVE ESTRATRIENES

[75] Inventors: Alain Jouquey; Gaëtan Touyer; Jean Salmon; Michel Mouren, all of Paris, France

[73] Assignee: Roussel Uclaf, Paris, France

[21] Appl. No.: 560,184

[22] Filed: Dec. 12, 1983

[30] Foreign Application Priority Data

Dec. 13, 1982 [FR] France ................... 82 20845

[51] Int. Cl.⁴ ................. A61K 49/00; A61K 43/00
[52] U.S. Cl. ........................ 424/1.1; 424/9; 424/85; 260/397.5; 260/397.45; 514/182
[58] Field of Search .............. 260/397.45, 397.5; 424/238, 1.1, 9, 85; 514/182

[56] References Cited

U.S. PATENT DOCUMENTS 4,323,511  4/1982  Varma et al. ............ 260/397.45
4,331,646  5/1982  Delaage ................. 260/239.5

OTHER PUBLICATIONS

"Steroids" (1978) vol. 31, No. 3, pp. 393–406, article by Scott et al.

Primary Examiner—Elbert L. Roberts
Attorney, Agent, or Firm—Bierman and Muserlian

[57] ABSTRACT

Novel radioactive $\Delta^{4,9,11}$-estratrienes marked with iodine 125 or 131 having the formula

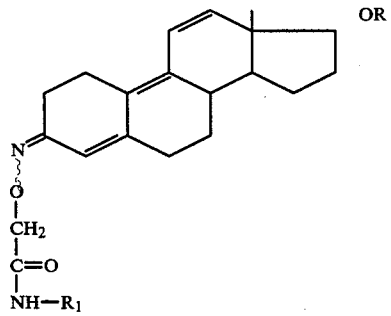

wherein R is selected from the group consisting of hydrogen, alkyl of 1 to 6 carbon atoms and acyl of an organic carboxylic acid of 2 to 12 carbon atoms, $R_1$ is the reminder of an amino acid of the formula $R_1NH_2$ or a derivative thereof being marked with iodine 125 or 131 and the wavy lines indicate the —OR is in the α- or β-position and the oximido group is in the syn or anti position, a process and intermediates for their preparation, antigens prepared therefrom and use thereof to prepare antibodies.

17 Claims, No Drawings

NOVEL RADIOACTIVE ESTRATRIENES

STATE OF THE ART

U.S. Pat. No. 4,339,390 describes radiolabeling of cortisol-21-acetate and British Pat. No. 1,604,864 relates to iodinating progesterone derivatives. French Pat. No. 2,397,426 radioactive steroids and French Pat. No. 2,250,745 describes methyl testosterone-3-(0-carboxymethyl)oximino-tyrosinate and its preparation.

OBJECTS OF THE INVENTION

It is an object of the invention to provide the radioactive iodine marked steroids of formula I and a process and novel intermediates for their preparation.

It is a further object of the invention to provide antigens of said radioactive iodine marked steroids of formula I and bovine seric albumin and human seric albumin.

It is an additional object of the invention to provide novel antibodies and their use.

These and other objects and advantages of the invention will become obvious from the following detailed description.

THE INVENTION

The novel radioactive $\Delta^{4,9,11}$-estratrienes marked with iodine 125 or 131 of the invention have the formula

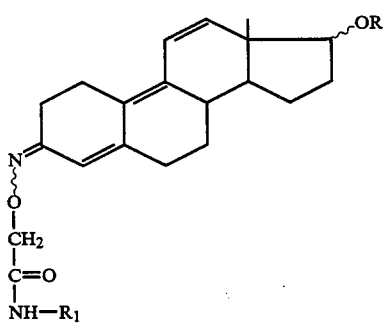

wherein R is selected from the group consisting of hydrogen, alkyl of 1 to 6 carbon atoms and acyl of an organic carboxylic acid of 2 to 12 carbon atoms, $R_1$ is the reminder of an amino acid of the formula $R_1NH_2$ or a derivative thereof being marked with iodine 125 or 131 and the wavy lines indicate the —OR is in the α- or β-position and the wavy line attached to the nitrogen indicates the syn or anti position.

The derivatives of the amino carboxylic acids are preferably a decarboxylated derivative or a lower alkyl ester of the amino acid. The preferred amino acids marked with radioactive iodine are selected from the group consisting of histidine, tyrosine, histamine, tyramine and methyl tyrosinate marked with $^{125}I$ or $^{131}I$.

Among the preferred compounds of formula I are the syn isomer of 3-carboxymethyloximino-$\Delta^{4,9,11}$-estratriene-17β-ol coupled with $^{125}I$ histamine of the formula

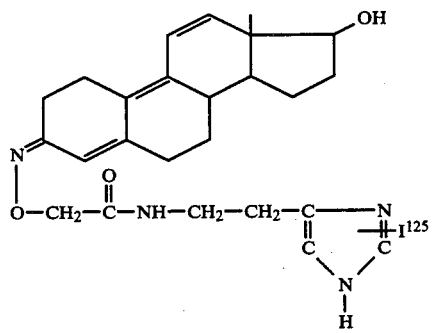

with the iodine in the 2- or 5-position; the anti isomer of 3-carboxymethyloximino-$\Delta^{4,9,11}$-estratriene-17β-ol coupled with $^{125}I$ histamine of the formula

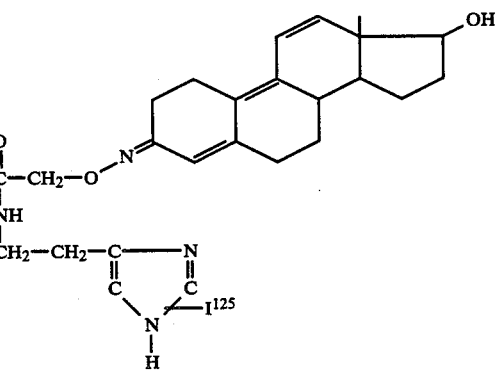

with the iodine in the 2- or 5-position; the syn isomer of 3-carboxymethyloximino-$\Delta^{4,9,11}$-estratriene-17α-ol coupled with $^{125}I$ histamine of the formula

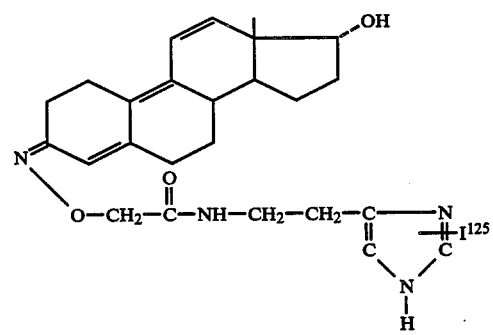

with the iodine in the 2- or 5-position; the anti isomer of 3-carboxymethyloximino-$\Delta^{4,9,11}$-estratriene-17α-ol coupled with $^{125}I$ histamine of the formula

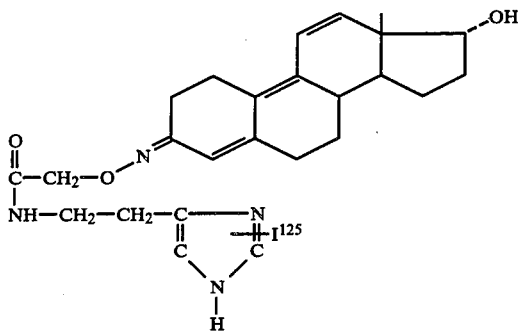

with the iodine in the 2- or 5-position; a mixture of the syn and anti isomers of 3-carboxymethyloximino-$\Delta^{4,9,11}$-estratriene-17β- or 17α-ol coupled with $^{125}$I histamine with the iodine in the 2- or 5-position.

The novel process of the invention for the preparation of the compounds of formula I comprises reacting a compound of the formula

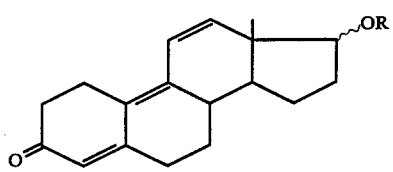

wherein R and the wavy line have the above definitions with a carboxymethoxyamine halide in the presence of a base to obtain a compound of the formula

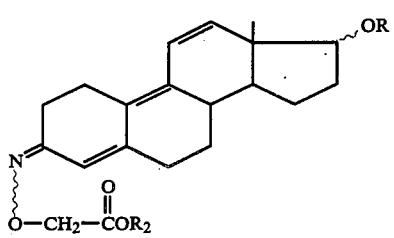

wherein the wavy line in the 17-position has the above definition and the wavy line attached to the nitrogen is a mixture of anti and syn isomers and $R_2$ is hydrogen and then either fixing the acid function of the product with an activator group of a carbonyl function to obtain a compound of the formula

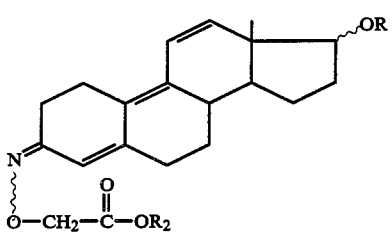

wherein $R_2$ is an activating group of the carbonyl function and the wavy line on the nitrogen indicates a mixture of syn and anti isomers and reacting the latter with an amino acid marked with $^{125}$I or $^{131}$I or a derivative thereof to obtain the corresponding compound of formula I as a mixture of the syn and anti isomers which can be optionally separated or reacting a compound of formula III$_A$ as a mixture of syn and anti isomers with an esterification agent of an alkanol of 1 to 6 carbon atoms to obtain a mixture of the syn and anti isomers of a compound of the formula

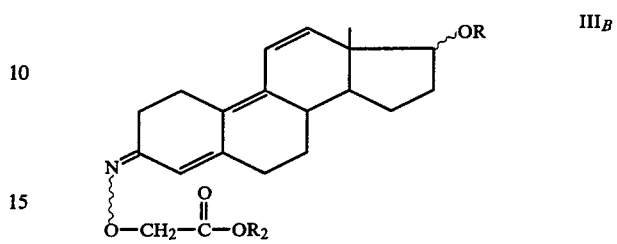

wherein $R_2$ is alkyl of 1 to 6 carbon atoms, separating the isomers, individually saponifying the said esters to obtain the compound of formula III$_A$ in the form of its individual anti and syn isomers wherein $R_2$ is hydrogen, fixing the acid group of the said isomers with a carbonyl activator to obtain the individual syn and anti isomers of the compound of formula III$_C$ wherein $R_2$ is the carbonyl activator function and reacting the latter with an amino acid marked with $^{125}$I or $^{131}$I or a derivative thereof to obtain the individual syn and anti isomers of formula I.

In a preferred process of the invention, the amino acid marked with iodine or a derivative thereof is selected from the group consisting of histidine, tyrosine, histamine, tyramine and methyl tyrosinate and the reaction of the compound of formula II is effected with carboxymethoxyamine hemihydrochloride in the dark under an inert atmosphere in the presence of sodium hydroxide. The fixing of the acid function with a carbonyl activator is preferably effected with an alkyl haloformate in the presence of a tertiary base under an inert atmosphere and anhydrous conditions which results in the formation of a group of the formula

wherein AlK is alkyl of 1 to 6 carbon atoms.

More preferably, the alkyl haloformate is isobutyl chloroformate and the reaction is effected in the presence of tri-n-butylamine. The esterification agent is diazomethane and the saponification of the ester group is effected with methanolic sodium hydroxide. The reaction of the compound of formula III$_C$ wherein $R_2$ is a carbonyl activating group is effected with histamine marked with $^{125}$I or $^{131}$I in the dark under an inert atmosphere. The activation of the carbonyl group of formula III$_A$ where $R_2$ is hydrogen is effected by N-hydroxysuccinimide or dicyclohexylcarbodiimide to generate the activated group of the carbonyl.

The more preferred embodiment of the process of the invention comprises reacting $\Delta^{4,9,11}$-estratriene-17β-ol-3-one or $\Delta^{4,9,11}$-estratriene-17α-ol-3-one to obtain a mixture of the corresponding syn and anti isomers or the individual syn or anti isomers of the formulae

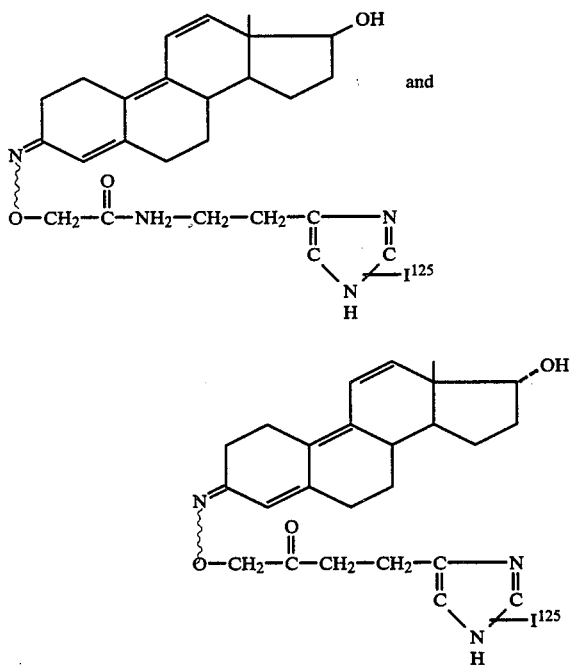

with iodine in the 2- or 5-position.

The compounds of formula I are useful for radioimmunological dosages of $\Delta^{4,9,11}$-estratriene-17α- and 17β-ols in bile, urine, feces, plasma and animal and human tissues and in foods of humans and warm-blooded animals.

The novel intermediates of the invention for the preparation of the compounds of formula I are the compounds in the form of syn and anti isomers and mixtures thereof of the formula

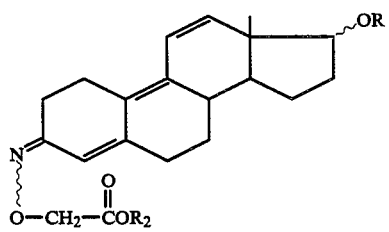

wherein R is hydrogen, alkyl of 1 to 6 carbon atoms or acyl of an organic carboxylic acid of 2 to 12 carbon atoms, $R_2$ is hydrogen, alkyl of 1 to 6 carbon atoms or a carbonyl activating group, the wavy line in the 17-position indicates the α- or β-position and the wavy line attached to the nitrogen indicates the syn or anti position. The carbonyl activator group is preferably —COOAlK with AlK being alkyl of 1 to 6 carbon atoms.

Among the preferred compounds of formula III are the syn and anti isomers and mixtures thereof of 3-carboxymethyloximino-$\Delta^{4,9,11}$-estratriene-17β-ol or 3-carboxymethyloximino-$\Delta^{4,9,11}$-estratriene-17α-ol or 3-carbethoxymethyloximino-$\Delta^{4,9,11}$-estratriene-17β-ol or 3-carbethoxymethyloximino-$\Delta^{4,9,11}$-estratriene-17α-ol, the mixed anhydride of isobutyl formate and 3-carboxymethyloximino-$\Delta^{4,9,11}$-estratriene-17β-ol in the form of its anti and syn isomers and mixtures thereof of the formula

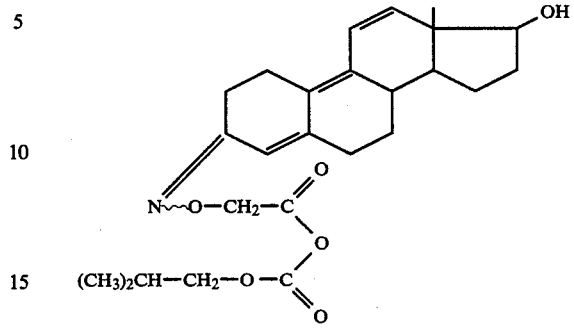

wherein the wavy line has the above definition and the mixed anhydride of isobutyl formate and 3-carboxymethyloximino-$\Delta^{4,9,11}$-estratriene-17α-ol in the form of its anti and syn isomers and mixtures thereof of the formula

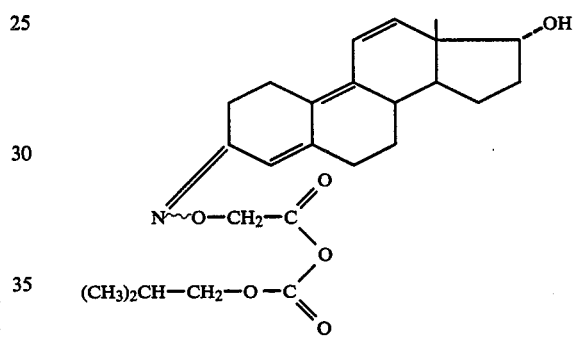

The compounds of formula III, especially those wherein $R_2$ is hydrogen, are useful starting compounds for the preparation of antigens, equally necessary for radioimmunological doses of $\Delta^{4,9,11}$-estratriene-17β- and 17α-ol-3-ones. The use of the compounds of formula III conjugated with bovine seric albumin (BSA) or human seric albumin (HSA) to obtain an antigen is also part of the invention.

In a preferred process of the invention for the preparation of antigens with the compounds of formula III in which $R_2$ is hydrogen comprises reacting a compound of formula III$_A$ in the form of its anti isomer or syn isomer or mixtures thereof when $R_2$ is hydrogen and R has the above definition after activation of the carbonyl function with an alkyl haloformate in the presence of a tertiary base under anhydrous conditions and an inert atmosphere to obtain a mixed anhydride of formula III$^C$ wherein $R_2$ is —COOAlK and AlK is alkyl of 1 to 6 carbon atoms and conjugating the latter with bovine seric albumin (BSA) or human seric albumin (HSA) to obtain the desired antigen.

In the preferred mode of the latter process, the compound of formula III is reacted with isobutyl chloroformate in anhydrous dioxane in the presence of tri-n-butylamine under an inert atmosphere and the mixed anhydride is reacted with a solution of bovine seric albumin or human seric albumin in a mixture of water and dioxane under an inert atmosphere.

Examples of preferred antigens starting from the syn or anti isomer or mixture thereof of 3-carboxymethyloximino-$\Delta^{4,9,11}$-estratriene-17$\beta$-OR are antigens of the formula

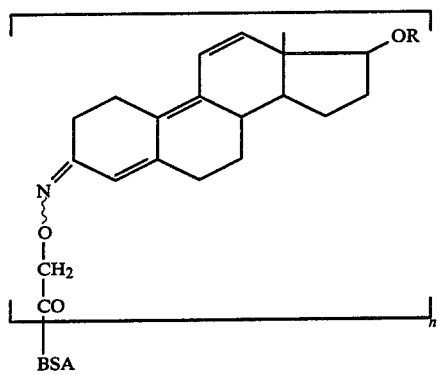

IV and

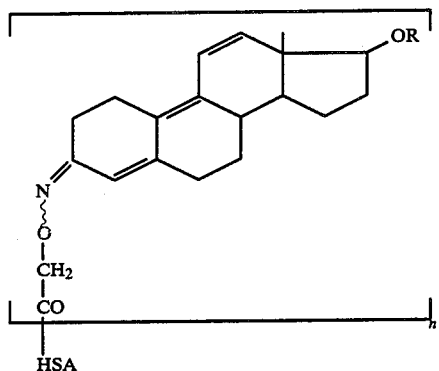

V wherein n is 20 to 30 and starting from 3-carboxymethyloximino-$\Delta^{4,9,11}$-estratriene-17$\alpha$-OR in the form of its anti or syn isomer or mixtures thereof are antigens of the formula

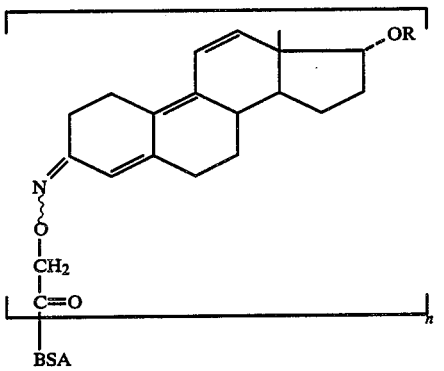

VI and

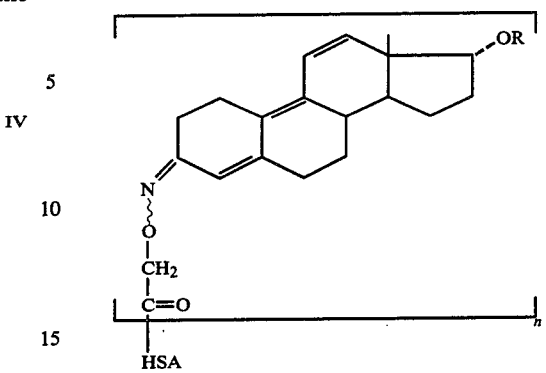

VII wherein n is 20 to 30. The antigens of formulae IV, V, VI and VII are a part of the invention.

The novel method of the invention for the preparation of antibodies comprises administering to warm-blooded animals an antigen of the invention in the presence of an adjuvant to obtain serum containing antibodies against $\Delta^{4,9,11}$-estratriene-17$\beta$-ol-3-one and $\Delta^{4,9,11}$-estratriene-17$\alpha$-ol.

The compounds of formula I and especially the syn and anti isomers and mixtures thereof of 3-carboxymethyloximino-$\Delta^{4,9,11}$-estratriene-17$\beta$-ol $^{125}$I histamine or 3-carboxymethyloximino-$\Delta^{4,9,11}$-estratriene-17$\alpha$-ol $^{125}$I histamine are used in radioimmuniological dosage of $\Delta^{4,9,11}$-estratriene-17$\alpha$- and 17$\beta$-ol-3-ones and permits dosages of these products in biological liquids and tissues and in human and animal alimentation. The radioimmunological dosage is effected by the method of Bergson et al [Hormone, Vol. 4 (1964), p. 557] and Abraham [Journal of Chemical Endocrinonal metab, Vol. 29 (1969), p. 866].

In the following examples there are described several preferred embodiments to illustrate the invention. However, it is to be understood that the invention is not intended to be limited to the specific embodiments.

EXAMPLE 1

Syn and anti isomers of 3-carboxymethyloximino-$\Delta^{4,9,11}$-estratriene-17$\beta$- and 17$\alpha$-ol STEP A: Syn and anti isomers of 3-carboxymethyloximino-$\Delta^{4,9,11}$-estratriene-17$\beta$-ol 3.05 g of carboxymethoxyamine hemihydrochloride and 15 ml of N sodium hydroxide solution were successively added under an inert atmosphere in the dark to a suspension of 3.29 g of $\Delta^{4,9,11}$-estratriene-17$\beta$-ol-3-one in 85 ml of ethanol and the mixture was stirred in the dark at room temperature for about 3 hours and was poured into iced water containing hydrochloric acid. The mixture was vacuum filtered and the product was washed with water until the wash water was neutral and dried under reduced pressure to obtain 3.86 g of product. The latter was chromatographed over silica gel and was eluted with a 90-10-1 methylene chloride-methanol-acetic acid mixture to obtain a mixture of syn and anti isomers of 3-carboxymethyloximino-$\Delta^{4,9,11}$-estratriene-17$\beta$-ol with an RF=0.35.

NMR Spectrum (90 MHz):
529 Hz (4-hydrogen of anti isomer); 558-584 Hz (4-hydrogen of masked syn isomer).

STEP B: Syn and anti isomers of 3-carboxymethyloximino-$\Delta^{4,9,11}$-estratriene-17α-ol Using the procedure of Step A, a mixture of 1.59 g of $\Delta^{4,9,11}$-estratriene-17α-ol-3-one, 40 ml of ethanol, 1.5 g of carboxymethoxyamine hemihydrochloride and 15 ml of N sodium hydroxide solution were reacted to obtain 1.75 g of product. The latter was chromatographed over silica gel and was eluted with a 7-3 cyclohexane-ethyl acetate mixture to obtain a mixture of the syn and anti isomers of 3-carboxymethyloximino-$\Delta^{4,9,11}$-estratriene-17α-ol with an Rf=0.25.

EXAMPLE 2

Separation of syn and anti isomers of 3-carboxymethyloximino-$\Delta^{4,9,11}$-estratriene-17β-ol STEP A: Syn and anti isomers of 3-carbethoxymethyloximino-$\Delta^{4,9,11}$-estratriene-17β-ol 25 ml of diazomethane were added with stirring at 0° C. under an inert atmosphere to a suspension of 1.3 g of a mixture of syn and anti isomers of 3-carboxymethyloximino-$\Delta^{4,9,11}$-estratriene-17β-ol in 20 ml of methylene chloride and the mixture was stirred for one hour at 0° C. The decanted organic phase was evaporated to dryness under reduced pressure to obtain 1.53 g of an oil product which was dissolved in 3 ml of ethyl acetate. The solution was chromatographed over silica gel and elution with a 1-1 cyclohexane-ethyl acetate mixture yielded 750 mg of the anti isomer of 3-carboxymethyloximino-$\Delta^{4,9,11}$-estratriene-17β-ol in the form of an ester with an Rf=0.32 and a second oil fraction of 350 mg of the syn isomer with an Rf=0.28. The separated isomers were saponified and analyzed in the acid form to confirm the syn and anti structures.

STEP B: Syn isomer of 3-carboxymethyloximino-$\Delta^{4,9,11}$-estratriene-17β-ol A mixture of 350 mg of the syn isomer of Step A, 5 ml of methanol and 1 ml of sodium hydroxide was stirred in the dark under an inert atmosphere at room temperature for one hour and the mixture was cooled to 0° C. and admixed with 1 ml of concentrated hydrochloric acid. The mixture was vacuum filtered and the product was dried under reduced pressure to obtain 295 mg of the syn isomer of 3-carboxymethyloximino-$\Delta^{4,9,11}$-estratriene-17β-ol.

NMR Spectrum (90 MHz):
570–590 Hz (4,-11- and 12-hydrogens of syn isomer)
UV Spectrum (ethanol):

| Inflex. towards | 313 nm | $E_1^1 = 883$ | |
| Max. at | 325 nm | $E_1^1 = 1144$ | $\epsilon = 39,300$ |
| Inflex. towards | 335 nm | $E_1^1 = 1098$ | |

Circular dichroism (ethanol):

| Max. at | 231 nm | $\Delta\epsilon = +2.75$ |
| Inflex. towards | 255 nm | $\Delta\epsilon = -2.25$ |
| Inflex. towards | 290 nm | $\Delta\epsilon = -2.7$ |
| Max. at | 302 nm | $\Delta\epsilon = -3.8$ |
| Max. at | 315 nm | $\Delta\epsilon = -4.5$ |
| Max. at | 331 nm | $\Delta\epsilon = 2.5$ |
| Max. at | 347 nm | $\Delta\epsilon = +1.3$ |

STEP C: Anti isomer of 3-carboxymethyloximino-$\Delta^{4,9,11}$-estratriene-17β-ol Using the procedure of Step B, the 750 mg of the anti isomer of Step A, 10 ml of methanol and 1.6 ml of sodium hydroxide were reacted to obtain 660 mg of the anti isomer of 3-carboxymethyloximino-$\Delta^{4,9,11}$-estratriene-17β-ol.

NMR Spectrum (90 MHz):
526 Hz (4-hydrogen of anti isomer).
UV Spectrum (ethanol):

| Inflex. towards | 310 nm | $E_1^1 = 855$ | |
| Inflex. towards | 335 nm | $E_1^1 = 1010$ | $\epsilon = 39,300$ |
| Max. at | 322 nm | $E_1^1 = 1144$ | |

Circular dichroism (ethanol):

| Max at | 231 nm | $\Delta\epsilon = +3.0$ |
| Max. at | 253 nm | $\Delta\epsilon = -1.05$ |
| Inflex. towards | 290 nm | $\Delta\epsilon = -2.7$ |
| Max. at | 300 nm | $\Delta\epsilon = -4.2$ |
| Max. at | 315 nm | $\Delta\epsilon = -4.6$ |
| Max. at | 329 nm | $\Delta\epsilon = -1.6$ |
| Max. at | 343 nm | $\Delta\epsilon = +2.75$ |

EXAMPLE 3

Syn and anti isomers of 3-carboxymethyloximino-$\Delta^{4,9,11}$-estratriene-17α-ol STEP A: 3-carbethoxymethyloximino-$\Delta^{4,9,11}$-estratriene-17α-ol Using the procedure of Step A of Example 2, 1.64 g of a mixture of the syn and anti isomers of 3-carboxymethyloximino-$\Delta^{4,9,11}$-estratriene-17α-ol of Example 1, 26 ml of methylene chloride and 35 ml of diazomethane were reacted to obtain 1.55 g of a mixture of syn and anti of 3-carboxymethyloximino-$\Delta^{4,9,11}$-estratriene-17α-ol. The mixture was chromatographed over silica gel and was eluted with a 7-3 cyclohexaneethyl acetate mixture obtain 580 mg of the presumed anti isomer with an Rf=0.17 and a second fraction of 490 mg of the presumed syn isomer with an Rf=0.13. The products were saponified and analyzed in the acid form.

STEP B: Anti isomer of 3-carboxymethyloximino-$\Delta^{4,9,11}$-estratriene-17α-ol Using the procedure of Step B of Example 2, 580 mg of the anti isomer of Step A, 7 ml of methanol and 1.3 ml of sodium hydroxide solution were reacted to obtain 440 mg of anti isomer of 3-carboxymethyloximino-$\Delta^{4,9,11}$-estratriene-17α-ol.

NMR Spectrum (90 MHz):
532 Hz (4-hydrogen of anti isomer)
UV Spectrum (1-4 ethanol-water):

| Inflex. towards | 312 nm | $E_1^1 = 874$ | |
| Max. at | 323 nm | $E_1^1 = 1132$ | $\epsilon = 39,000$ |
| Inflex. towards | 335 nm | $E_1^1 = 1010$ | |

Circular Dichroism (1-4 ethanol-water):

| Max. at 251 nm | $\Delta\epsilon = -2.4$ |
| Max. at 303 nm | $\Delta\epsilon = -2.9$ |
| Max. at 315 nm | $\Delta\epsilon = -2.8$ |
| Max. at 349 nm | $\Delta\epsilon = +2.8$ |

STEP C: Syn isomer of 3-carboxymethyloximino-$\Delta^{4,9,11}$-estratriene-17α-ol Using the procedure of Step C of Example 2, 490 mg of the presumed syn isomer of Step A, 6,5 ml of methanol and 1,1 ml of sodium hydroxide solution were reacted to obtain 325 mg of syn isomer of 3-carboxymethyloximino-$\Delta^{4,9,11}$-estradiene-17α-ol.

NMR Spectrum (90 MHz):
532 Hz for $H_2$
585 Hz for $H_4$ of syn isomer

UV Spectrum (1-4 ethanol-water)

| | | |
|---|---|---|
| infl. | 312 nm | $E_1^1 = 888$ |
| max. | 325 nm | $E_1^1 = 1168$ |
| infl. | 335 nm | $E_1^1 = 1136$ |

Circular dichroism (1-4 ethanol-water)

| | | |
|---|---|---|
| max. | 250 nm | $\Delta\epsilon = -3.3$ |
| max. | 303 nm | $\Delta\epsilon = -3.0$ |
| max. | 316 nm | $\Delta\epsilon = -3.1$ |
| max. | 350 nm | $\Delta\epsilon = +2.6$ |

EXAMPLE 4

Antigens of seric bovine albumin (BSA) and anti isomer of 3-carboxymethyloximino-$\Delta^{4,9,11}$-estratriene-17β-ol 0.23 ml of tri-n-butylamine were added with stirring under an inert atmosphere to a solution of 170 mg of the anti isomer of 3-carboxymethyloximino-$\Delta^{4,9,11}$-estratriene-17β-ol in 5 ml of dioxane and after reducing the temperature towards 13° C., 0.65 ml of isobutyl chloroformate were added thereto. The mixture was stirred at 13° C. for 30 minutes to obtain a solution of the mixed anhydride of isobutyl chloroformate and 3-carboxymethyloximino-$\Delta^{4,9,11}$-estratriene-17β-ol.

2 ml of dioxane were added with stirring under an inert atmosphere to a solution of 690 mg of BSA in 20 ml of iced water and the solution was stirred for 20 minutes. Then 20 ml of dioxane and then 0.7 ml of N sodium hydroxide solution were successively added to the mixture and the mixed anhydride solution was added to the BSA solution. The mixture was stirred at 4° C. for four hours and then 50 ml of distilled water were added thereto. The pH of the mixture was adjusted to 4.1 by addition of N hydrochloric acid. The mixture was filtered and the solid product was taken up in 50 ml of aqueous 1% sodium bicarbonate solution. The resulting solution was subjected to ultra filtrations and then passed 505 ml of water to extract the compounds with a molecular weight <10 to 15,000. The volume was adjusted to 23 ml and the solution was subjected to lyophilization for 24 hours to obtain 759 mg of antigens of seric bovine albumin (BSA) and anti isomer of 3-carboxymethyloximino-$\Delta^{4,9,11}$-estratriene-17β-ol having 24 to 25 steroid groups per mole.

UV Spectrum (water in presence of dioxane):

| | |
|---|---|
| Max. at 325 nm | $E_1^1 = 125$ |
| Inflex. towards 339 nm | $E_1^1 = 98$ |

Circular Dichroism (water in presence of dioxane):

| | |
|---|---|
| Max. at 209 nm | $\Delta E_1^1 = -0.350$ |
| Max. at 220 nm | $\Delta E_1^1 = -0.305$ |
| Max. at 335 nm | $\Delta E_1^1 = -0.020$ |

EXAMPLE 5

Antigen of BSA and the anti isomer of 3-carboxymethyloximino-$\Delta^{4,9,11}$-estratriene-17α-ol Using the procedure of Example 4, 170 mg of 3-carboxymethyloximino-$\Delta^{4,9,11}$-estratriene-17α-ol and 690 mg of BSA were reacted to obtain 912 mg of antigen of BSA and the anti isomer of 3-carboxymethyloximino-$\Delta^{4,9,11}$-estratriene-17α-ol having 22 to 23 steroid groups per mole.

UV Spectrum (water in presence of dioxane):

| | |
|---|---|
| Max. at 325 nm | $E_1^1 = 111$ |
| Inflex. towards 340 nm | $E_1^1 = 89$ |

Circular dichroism:

| | |
|---|---|
| Max. at 213 nm | $\Delta E_1^1 = -0.328$ |
| Max. at 223 nm | $\Delta E_1^1 = -0.324$ |
| Max. at 305 nm | $\Delta E_1^1 = -0.010$ |
| Max. at 316 nm | $\Delta E_1^1 = -0.009$ |
| Max. at 351 nm | $\Delta E_1^1 = +0.011$ |

EXAMPLE 6

Antigen of BSA and syn isomer of 3-carboxymethyloximino-$\Delta^{4,9,11}$-estratriene-17α-ol Using the procedure of Example 4, 170 mg of the syn isomer of 3-carboxymethyloximino-$\Delta^{4,9,11}$-estratriene-17β-ol and 690 mg of BSA were reacted to obtain 902 mg of the antigen of BSA and syn isomer of 3-carboxymethyloximino-$\Delta^{4,9,11}$-estratriene-17β-ol containing 22 to 24 steroid groups per mole.

UV Spectrum (water in presence of dioxane):

| | |
|---|---|
| Max. at 325 nm | $E_1^1 = 118$ |
| Inflex. towards 340 nm | $E_1^1 = 100$ |

Circular dichroism:

| | |
|---|---|
| Max. at 210 nm | $\Delta E_1^1 = -0.396$ |
| Max. at 222 nm | $\Delta E_1^1 = -0.010$ |
| Max. at 317 nm | $\Delta E_1^1 = -0.009$ |
| Max. at 351 nm | $\Delta E_1^1 = +0.012$ |

EXAMPLE 7

Antigen of BSA and syn isomer of 3-carboxymethyloximino-$\Delta^{4,9,11}$-estratriene-17β-ol Using the procedure of Example 4, BSA and the syn isomer of 3-carboxymethyloximino-$\Delta^{4,9,11}$-estratriene-17β-ol were reacted to form the antigen of BSA and syn isomer of 3-carboxymethyloximino-$\Delta^{4,9,11}$-estratriene-17β-ol.

EXAMPLE 8

Using the procedure of Example 4 an antigen was prepared from a mixture of the syn and anti isomers of 3-carboxymethyloximino $\Delta^{4,9,11}$-estratriene-17β and 17β-ols and BSA.

EXAMPLE 9

Using the procedure of Example 4, an antigen was prepared from a mixture of the syn and anti isomers of 3-carboxymethyloximino-$\Delta^{4,9,11}$-estratriene-17α- and 17β-ols and human seric albumin (HSA) as well as the antigens of HSA and the individual syn and anti isomers thereof.

EXAMPLE 10

Couple of ($I^{125}$) histamine and 3-carboxymethyloximino-$\Delta^{4,9,11}$-estratriene-17β-ol 10 ml of 1-5 tri-n-butylamine-tetrahydrofuran mixture and 10 ml of 1-10 isobutyl chloroformate-tetrahydrofuran mixture were added with cooling under an inert atmosphere with stirring to a solution of 2.4 mg of a mixture of the syn and anti isomers of 3-carboxymethyloximino-$\Delta^{4,9,11}$-estratriene-17β-ol in 50 ml of tetrahydrofuran and the mixture was stirred with cooling for 30 minutes. 3.4 ml of tetrahydrofuran were added to the mixture to obtain a solution of the mixed anhydride of isobutyl chloroformate and the syn and anti isomer mixture of 3-carboxymethyloximino-$\Delta^{4,9,11}$-estratriene-17β-ol which was used infra.

1 mCi of sodium iodide $^{125}$I (specific activity of 2000 Ci mmol) and then 50 μg of chloroamine T in 10 μl of distilled water were successively added to 10 μl of a solution of 2 mM of histamine in a buffered solution of 0.5M sodium phosphate with a pHof 8 and the mixture was stirred for about 90 seconds. A solution of 300 μg of sodium metabisulfate in 10 μl of distilled water were added to the mixture to obtain a solution of ($^{125}$I) histamine with an Rf=0.1 (chromatography over silica gel-elution with a 98-2 methanoltriethylamine mixture) which was used infra.

50 μl of the mixed anhydride solution were added to the $^{125}$I histamine solution and the mixture was stirred in the dark at about 4° C. for one hour. The mixture was diluted with 0.4 ml of 0.1M aqueous sodium bicarbonate-solution and was extracted with 1.5 ml of methylene chloride. The organic phase was evaporated to dryness and the residue was subjected to high performance liquid chromatography. Elution with a 97-3 chloroform-methanol mixture yielded a first peak of the couple of $^{125}$I histamine and the anti isomer of 3-carboxymethyloximino-$\Delta^{4,9,11}$-estratriene-17β-ol with a retention time 38 minutes and a second peak of the couple of $^{125}$I histamine and the syn isomer of 3-carboxymethyloximino-$\Delta^{4,9,11}$-estratriene-17β-ol with a retention time of 42 minutes. The couple of the anti isomer had a total activity of 150 μCi and the couple of the syn isomer had a total activity of 50 μCi.

EXAMPLE 11

Couple of $^{125}$I histamine and 3-carboxymethyloximino-$\Delta^{4,9,11}$-estratriene-17β-ol Using the procedure of Example 9, 2.4 mg of a mixture of the syn and anti isomers of 3-carboxymethyloximino-$\Delta^{4,9,11}$-estratriene-17β-estratriene-17β-ol, 50 ml of tetrahydrofuran and 10 ml of 1-10 isobutyl chloroformate-tetrahydrofuran mixture were reacted to form a solution of the mixed anhydride and 50 μl of the solution were reacted with a $^{125}$I histamine solution of Example 9 to obtain a couple of the $^{125}$I histamine and the anti and syn isomers. The residue was subjected to high performance liquid chromatography to obtain a first peak of the couple of $^{125}$I histamine and the anti isomer of 3-carboxymethyloximino-$\Delta^{4,9,11}$-estratriene-17β-ol with a retention time of 34 minutes and a second peak of the couple of $^{125}$I histamine and the syn isomer with a retention time of 42 minutes. The couple of the anti isomer had a total activity of 50 μCi and the couple of the syn isomer had a total activity of 150 μCi.

Various modifications of the products and processes of the invention may be made without departing from the spirit or scope thereof and it is to be understood that the invention is intended to be limited only as defined in the appended claims.

What we claim is:

1. A radioactive $\Delta^{4,9,11}$-estratriene marked with iodine 125 or 131 having the formula

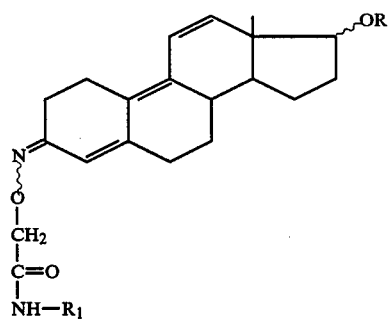

wherein R is selected from the group consisting of hydrogen, alkyl of 1 to 6 carbon atoms and acyl of an organic carboxylic acid of 2 to 12 carbon atoms, $R_1$ is the reminder of an amino acid of the formula $R_1NH_2$ or a derivative thereof being marked with iodine 125 or 131 and the wavy lines indicate the —OR is in the α- or β-position and the oximido group is in the syn or anti position.

2. A compound of claim 1 wherein the amino acid marked with iodine $^{125}$I or $^{131}$I is selected from the group consisting of histidine, tyrosine, histamine, tyramine and methyl tyrosinate.

3. A compound of claim 1 in the form of the syn isomer of 3-carboxymethyloximino-$\Delta^{4,9,11}$-estratriene-17β-ol coupled with $^{125}$I histamine of the formula

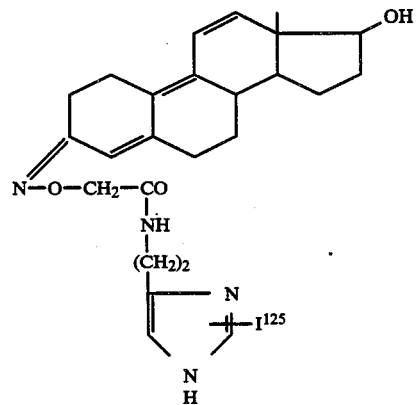

wherein the iodine is in the 2- or 5-position.

4. A compound of claim 1 in the form of the anti isomer of 3-carboxymethyloximino-$\Delta^{4,9,11}$-estratriene-17β-ol coupled with $^{125}$I histamine of the formula wherein the iodine is in the 2- or 5-position.

5. A compound of claim 1 in the form of the syn isomer of 3-carboxymethyloximino-Δ$^{4,9,11}$-estratriene-17α-ol coupled with $^{125}$I histamine of the formula wherein the iodine is in the 2- or 5-position.

6. A compound of claim 1 in the form of the anti isomer of 3-carboxymethyloximino-Δ$^{4,9,11}$-estratriene-17α-ol coupled with $^{125}$I histamine of the formula wherein the iodine is in the 2- or 5-position.

7. A mixture of claim 1 of the syn and anti isomers of 3-carboxymethyloximino-Δ$^{4,9,11}$-estratriene-17α- or 17β-ol coupled with $^{125}$I histamine with the iodine in the 2- or 5-position.

8. A process for the preparation of a compound of claim 1 comprising reacting a compound of the formula wherein R and the wavy line have the above definitions with a carboxymethoxyamine halide in the presence of a base to obtain a compound of the formula wherein the wavy line in the 17-position has the above definition and the wavy line attached to the nitrogen is a mixture of anti and syn isomers and $R_2$ is hydrogen and then either fixing the acid function of the product with an activator group of a carbonyl function to obtain a compound of the formula wherein $R_2$ is an activating group of the carbonyl function and the wavy line on the nitrogen indicates a mixture of syn and anti isomers and reacting the latter with an amino acid marked with $^{125}$I or $^{131}$I or a derivative thereof to obtain the corresponding compound of formula I as a mixture of the syn and anti isomers which can be optionally separated or reacting a compound of formula III$_A$ as a mixture of syn and anti isomers with an esterification agent of an alkanol of 1 to 6 carbon atoms to obtain a mixture of the syn and anti isomers of a compound of the formula wherein $R_2$ is alkyl of 1 to 6 carbon atoms, separating the isomers, individually saponifying the said esters to obtain the compoound of formula $III_A$ in the form of its individual anti and syn isomers wherein $R_2$ is hydrogen, fixing the acid group of the said isomers with a carbonyl activator to obtain the individual syn and anti isomers of the compound of formula $III_C$ wherein $R_2$ is the carbonyl activator function and reacting the latter with an amino acid marked with $^{125}I$ or $^{131}I$ or a derivative thereof to obtain the individual syn and anti isomers of formula I.

9. The process of claim 8 wherein the amino acid marked with iodine $^{125}I$ or $^{131}I$ is selected from the group consisting of histidine, tyrosine, histamine, tyramine and methyl tyrosinate.

10. The process of claim 8 wherein the starting material is $\Delta^{4,9,11}$-estratriene-17β-ol-3-one or $\Delta^{4,9,11}$-estratriene-17α-ol-3-one resulting in a mixture of the corresponding syn and anti isomers or the individual syn and anti isomers of the formula

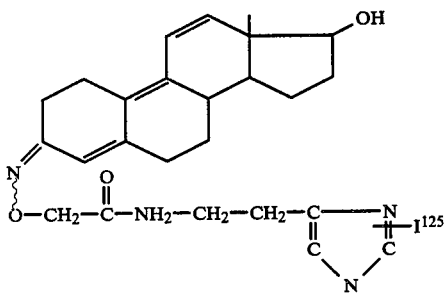

and

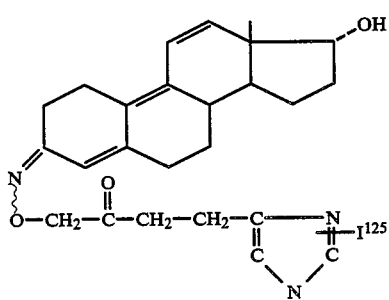

with iodine in the 2- or 5-position.

11. A process comprising administering to warm-blooded animals a radioimmunological dose of a compound of claim 1 and determining the amount of $\Delta^{4,9,11}$-estratriene-17β- and 17α-ol-3-one in the animal or human biological liquids and tissues and alimentation.

12. A compound in the form of syn and anti isomers and mixtures thereof of the formula

III

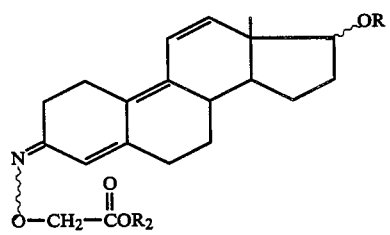

wherein R is hydrogen, alkyl of 1 to 6 carbon atoms or acyl of an organic carboxylic acid of 2 to 12 carbon atoms, $R_2$ is hydrogen, alkyl of 1 to 6 carbon atoms or a carbonyl activating group, the wavy line in the 17-position indicates the α- or β-position and the wavy line attached to the nitrogen indicates the syn or anti position.

13. A compound of claim 12 selected from the group consisting of the syn and anti isomers and mixtures thereof of 3-carboxymethyloximino-$\Delta^{4,9,11}$-estratriene-17β-ol or 3-carboxymethyloximino-$\Delta^{4,9,11}$-estratriene-17α-ol or 3-carbethoxymethyloximino-$\Delta^{4,9,11}$-estratriene-17β-ol or 3-carbethoxymethyloximino-$\Delta^{4,9,11}$-estratriene-17α-ol, the mixed anhydride of isobutyl formate and 3-carboxymethyloximino-$\Delta^{4,9,11}$-estratriene-17β-ol in the form of its anti and syn isomers and mixtures thereof of the formula

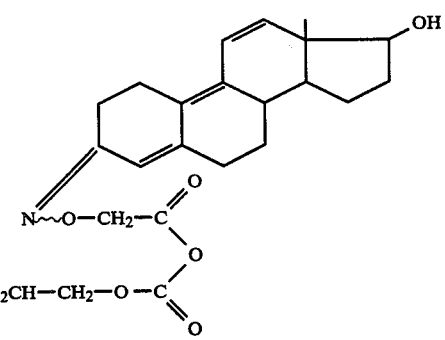

wherein the wavy lines have the above definitions and the mixed anhydride of isobutyl formate and 3-carboxymethyloximino-$\Delta^{4,9,11}$-estratriene-17α-ol in the form of its anti and syn isomers and mixtures thereof of the formula

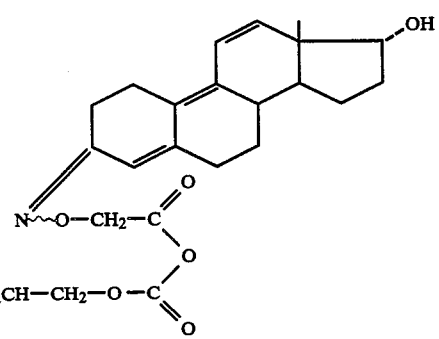

14. An antigen comprising a compound of claim 12 wherein $R_2$ is hydrogen conjugated with human seric albumin or bovine seric albumin.

15. A process of the preparation of an antigen of claim 14 comprising reacting a compound of claim 12 in the form of its anti isomer or syn isomer of mixtures thereof wherein $R_2$ is hydrogen and R has the above definition after activation of the carbonyl function with an alkyl haloformate in the presence of a tetriary base under anhydrous conditions and an inert atmosphere to obtain a mixed anhydride of formula $III_C$ wherein $R_2$ is —COOAlK and AlK is alkyl of 1 to 6 carbon atoms and conjugating the latter with bovine seric albumin (BSA) or human seric albumin (HSA) to obtain the desired antigen.

16. An antigen of claim 14 selected from the group consisting of syn or anti isomers and mixtures thereof of the formula

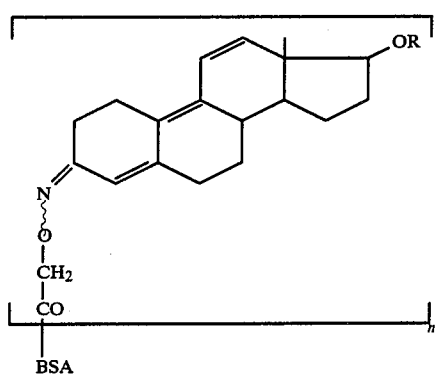
and
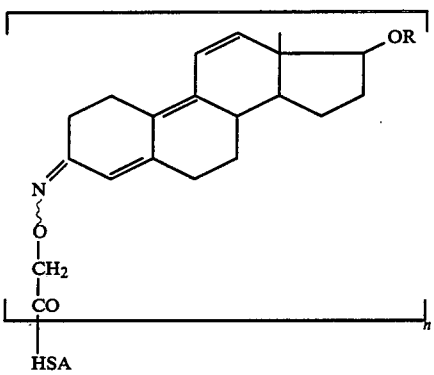
-continued
and
wherein n is 20 to 30.
17. A method of preparing antibodies comprising administering to warm-blooded animals an effective amount of an antigen of claim 14 in the presence of an adjuvant to obtain serum containing antibodies against $\Delta^{4,9,11}$-estratriene-17$\beta$-ol-3-one and $\Delta^{4,9,11}$-estratriene-17$\alpha$-ol.
* * * * *